United States Patent [19]

Laffan

[11] Patent Number: 5,364,946
[45] Date of Patent: Nov. 15, 1994

[54] PROCESS FOR THE PREPARATION OF SUBSTITUTED PENTAALKYLCHROMENES

[75] Inventor: David Laffan, Visp, Switzerland

[73] Assignees: Lonza Ltd., Gampel/Valais, Switzerland; Sankyo Company Ltd., Tokyo, Japan

[21] Appl. No.: 977,157

[22] Filed: Nov. 16, 1992

[30] Foreign Application Priority Data

Nov. 20, 1991 [CH] Switzerland .................. 3392/91

[51] Int. Cl.$^5$ ........................................ C07D 311/04
[52] U.S. Cl. ................................................ 549/407
[58] Field of Search ........................................ 549/407

[56] References Cited

FOREIGN PATENT DOCUMENTS 0139421 5/1985 European Pat. Off. .
2055097 2/1991 United Kingdom .

OTHER PUBLICATIONS

J. Med. Chem., 32, (1989), pp. 421 to 428.

*Primary Examiner*—Johann Richter
*Assistant Examiner*—Kimberly J. Kestler
*Attorney, Agent, or Firm*—Fisher, Christen & Sabol

[57] ABSTRACT

A novel process the preparation of pentaalkylchromenes of the general formula:

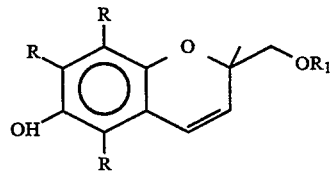

wherein R denotes a lower alkyl group having 1 to 4 C atoms and $R_1$ denotes a phenyl group which is unsubstituted or substituted by a lower alkyl group having 1 to 4 C atoms, by halogen or by a nitro group, or an alkanoyl group having 1 to 4 C atoms. In the process, a trialkylhydroquinone is reacted with a halogenated butenol to give a substituted tetraalkyhydroquinone, which is oxidized. Then the halogen atom is substituted with a suitable nucleophile and the compound is finally cyclized to give the final product. The pentaalkylchromenes are suitable intermediates for the preparation of hypolipidaemic pharmaceuticals.

16 Claims, No Drawings

PROCESS FOR THE PREPARATION OF SUBSTITUTED PENTAALKYLCHROMENES

BACKGROUND OF THE INVENTION

1. Field Of The Invention

The invention relates to a novel process for the preparation of pentaalkylchromenes of the general formula:

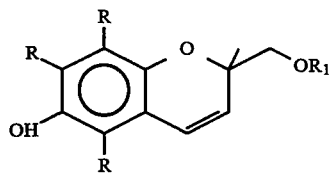

wherein R denotes a lower alkyl group having 1 to 4 C atoms and $R_1$ denotes a phenyl group which is unsubstituted or substituted by a lower alkyl group having 1 to 4 C atoms, by halogen or by a nitro group or an alkanoyl group having 1 to 4 C atoms, and to novel intermediates occurring in the process.

Pentaalkylchromenes, in particular tetramethylchromenes, are useful intermediates for the preparation of, for example, hypolipidaemic pharmaceuticals [*J. Med. Chem.*, 32, (1989), 428].

2. Background Art

European Published Patent Specification No. 139,421 discloses the preparation of corresponding pentaalkylchromenes by condensation of an acetylhydroquinone with alkoxy- or aryloxyacetone derivatives and by reduction of the resultant chromanone. This synthesis has the disadvantage that even the starting materials are accessible with difficulty, and additionally further steps are necessary after the condensation in order to obtain the desired pentaalkylchromene.

BROAD DESCRIPTION OF THE INVENTION

The main objective is to provide a novel process, which does not have the above-mentioned disadvantages, for the production of the pentaalkylchromenes of the general formula I. Other objectives and advantages of the invention are set out herein or are obvious herefrom to one skilled in the art.

The objectives and advantages of the invention are achieved by the process and the intermediates of the invention.

The invention involves a process for the preparation of substituted pentaalkylchromenes of the general formula:

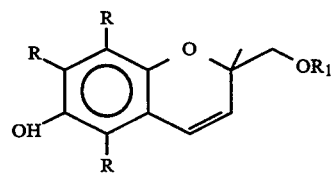

wherein R denotes a lower alkyl group having 1 to 4 C atoms and $R_1$ denotes a phenyl group which is unsubstituted or substituted by a lower alkyl group having 1 to 4 C atoms, by halogen or by a nitro group, or an alkanoyl group having 1 to 4 C atoms. In the first step (a), according to the invention process, a trialkylhydroquinone of the general formula:

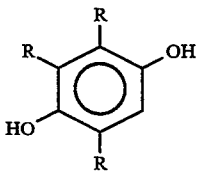

wherein R has the above-stated meaning, is reacted with halogenated butenols of the formula:

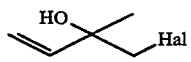

or

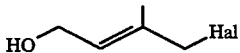

wherein Hal denotes chlorine, bromine or iodine, in the presence of a Lewis acid, such that a tetraalkylhydroquinone of the general formula:

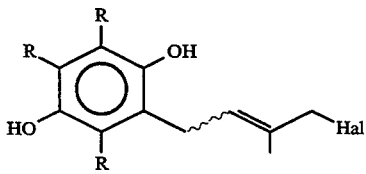

wherein R and Hal have the above-stated meanings, results as an intermediate. These compounds have not been described until now and are likewise part of the invention. The tetraalkylhydroquinone IV is cyclized to the final product (of the general formula I).

The invention also includes the quinones of the general formula:

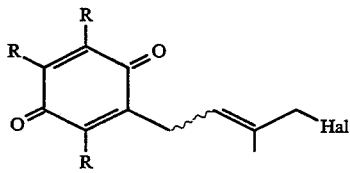

wherein R denotes a lower alkyl group having 1 to 4 C atoms and Hal denotes a chlorine, bromine or iodine. Preferably the quinone of the formula V is 2-(1-chloro-2-methylbut-2-en-4-yl)-3,5,6-trimethyl-1,4-benzoquinone of the formula:

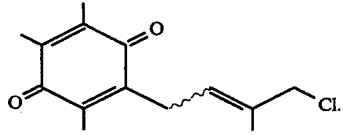

DETAILED DESCRIPTION OF THE INVENTION

Preferably, trimethylhydroquinone (formula II where R is $CH_3$) is reacted with 1-chloro-2-methylbut-3-en-2-ol (formula IIIa where Hal is Cl) to give the corresponding tetraalkylhydroquinone (formula IV where R is CH₃ and Hal is Cl).

The Lewis acid expediently employed is iron chloride, tin trifluoromethanesulfonate or boron trifluoride or one of its complexes, preferably boron trifluoride or one of its complex compounds, such as, boron trifluoride etherate. The Lewis acid is expediently employed in an amount from 1 mol to 5 mol, relative to trialkylhydroquinone employed. The reaction is advantageously carried out in the presence of an inert solvent, such as, in aromatic compounds, for example, in toluene or in halogenated hydrocarbons, for example, in methylene chloride, at a temperature between −10° and 50° C., preferably at room temperature.

The process is preferably carried out in such a way that, when starting material (trialkylhydroquinone) is virtually no longer detectable in the reaction mixture, the reaction is immediately stopped and the resultant tetraalkylhydroquinone is isolated.

The tetraalkylhydroquinone is oxidized in the second step (b) with air or oxygen to the quinone of the general formula:

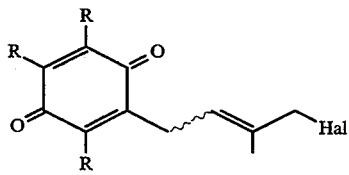

V wherein R and Hal have the above-stated meaning. Preferably, the oxidation is carried out with oxygen. The oxidation advantageously takes place at room temperature in the presence of an inert solvent. The reaction is usually quantitative.

The resultant quinones of the general formula V have not been described until now and are therefore likewise part of the invention. A preferred quinone of the general formula V is 2-(1-chloro-2-methylbut-2-en-4-yl)-3,5,6-trimethyl-1,4-benzoquinone where R is CH₃ and Hal is Cl.

In the subsequent third step (c), the halogen atom in the quinone of the general formula V is nucleophilically substituted with a nucleophilic compound of the general formula:

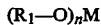 VI wherein R₁ has the above-stated meaning, M denotes an alkali metal or alkaline earth metal atom and n is 1 or 2, to give a quinone of the general formula:

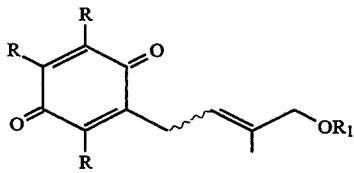

VII

Suitable nucleophilic compounds of the general formula VI are the alkali metal or alkaline earth metal salts of the C₁–C₄-carboxylic acids, preferably acetic acid, or substituted phenols, preferably p-nitrophenol. Depending on the solubility of the reaction components, the reaction is carried out in the presence of a suitable phase transfer catalyst. Expediently, tetraalkylammonium halides or tetraalkylphosphonium halides, such as, tetrabutylammonium iodide, are used for this purpose. The phase transfer catalysts are expediently employed in an amount from 0.05 mol to 1 mol, relative to the employed quinone of the general formula V. The reaction expediently takes place in the presence of a polar solvent, such as, in the presence of acetonitrile or methylene chloride at a temperature between 0° C. and the boiling temperature (reflux temperature) of the particular solvent, preferably at reflux temperature. The resultant nucleophilically substituted quinone of the general formula VII is preferably not isolated, but cyclized directly to give the final product according to step (d).

The cyclization can be carried out either thermally, by acid catalysis or by base catalysis. Expediently, cyclization is by acid or base catalysis. If cyclization by acid catalysis is selected, the reaction is expediently carried out in the presence of a mineral acid, such as, sulfuric acid. Preferably, the cyclization is carried out by base catalysis with a trialkylamine, such as, triethylamine in an amount from 0.1 mol to 2 mol. Expediently, the reaction is carried out in the polar solvent already used for the substitution, preferably under reflux conditions.

The resultant pentaalkylchromene of the general formula I can be isolated from the reaction mixture in a manner known to a person skilled in the art.

EXAMPLE (a) Process for the preparation of 2-(1-chloro-2-methylbut-2-en-4-yl)-1,4-dihydroxy-3,5,6-trimethylbenzene Trimethylhydroquinone (2.00 g, 14 mol) was suspended at room temperature in a mixture of chlorobenzene (10 ml) and hexane (5 ml). Boron trifluoride diethyl ether complex (3.60 ml of a 48 percent strength solution of boron trifluoride in diethyl ether, 1.95 g of boron trifluoride, 28 mmol) was then added in the course of 15 min. 1-Chloro-2-methylbut-3-en-2-ol (2.42 g, 20 mmol) was then added dropwise in the course of 15 min. After 30 min.,, the reaction mixture was filtered, and the filtrate was washed with chlorobenzene (10 mol) and dried at 40° C./20 mbar for 8 hours. 2.24 g (62.9 percent) of 2-(1-chloro-2-methylbut-2-en-4-yl)-1,4-dihydroxy-3,5,6-trimethylbenzene were obtained. The melting point of the product was 118° to 122° C. (decomposition). Other data regarding the product was:

¹H-NMR: (CDCl₃, 300 MHz) δ in ppm: 5.50 (t, 1H, J=7.5 Hz); 4.02 (s, 2H); 3.45 (d, 2H, J=7.5 Hz); 2.17 (s, 6H); 2.15 (s, 3H); 1.95 (s, 3H).

Isomer: 5.48 (t, 1H, J=7.5 Hz); 4.02 (s, 2H); 3.48 (d, 2H, J=7.5 Hz); 2.17 (s, 6H); 2.15 (s, 3H); 1.95 (s, 3H).

(b) Process for the preparation of 2-(1-chloro-2,methylbut-2-en,4-yl)-3,5,6-trimethyl-1,4-benzoquinone 2-(1-Chloro-2-methylbut-2-en-4-yl)-1,4-dihydroxy-3,5,6-trimethylbenzene (5.6 g, 22.0 mol) was suspended in chloroform (100 ml) at room temperature. Oxygen [O₂ (g)] was passed in. After 4 hours, the addition of oxygen was stopped, the reaction mixture was filtered and the mother liquor was concentrated.

This gave 2-(1-chloro-2-methylbut-2-en-4-yl)-3,5,6-trimethyl-1,4-benzoquinone (5.6 g, 99 percent). Data regarding the product was:

$^1$H-NMR: (CDCl$_3$, 300 MHz) δ in ppm: 5.38 (t, 1H, J=7.5 Hz); 3.99 (s, 2H); 3.26 (d, 2H, J=7.5 Hz); 2.05 (s, 3H); 2.02 (s, 6H); 1.90 (s, 3H).

Isomer: 5.25 (t, 1H, J=7.5 Hz); 4.24 (s, 2H); 3.29 (d, 2H, J=7.5 Hz); 2.08 (s, 3H); 2.02 (s, 6H); 1.90 (s, 3H).

(c) Process for the preparation of 6-hydroxy-2-(4-nitrophenoxymethyl)-2,5,7,8-tetramethylchromo-3-ene 2-(1-Chloro-2-methylbut-2-en-4-yl)-3,5,6,-trimethyl-1,4-benzoquinone (2.53 g, 10 mmol) was treated in acetonitrile with sodium p-nitrophenolate (1.95 g, content 82.7 percent, 10 mmol) and tetrabutylammonium iodide (0.37 g, 1 mmol) and heated to reflux. After 1 hour, triethylamine (1.0 g, 10 mmol) was added. After 5 hours, the mixture was cooled to room temperature and then filtered with suction. 6-Hydroxy-2-(4-nitrophenoxyphenyl)-2,5,7,8-tetramethylchrom-3-ene was isolated by chromatography. Data regarding the product was:

$^1$H-NMR: (CDCl$_3$, 300 MHz) δ in ppm: 8.15 (d, 2H, J=8 Hz); 6.95 (d, 2H, J=8 Hz); 6.70 (d, 1H, J=9 Hz); 5.72 (d, 1H, J=9 Hz); 4.28 (s, 1H); 4.11 (d, 1H, J=10 Hz); 4.03 (d, 1H, J=10 Hz); 2.21 (s, 3H); 2.15 (s, 3H); 2.06 (s, 3H); 1.56 (s, 3H).

What is claimed is:

1. A process for the preparation of a substituted pentaalkylchromene of the formula:

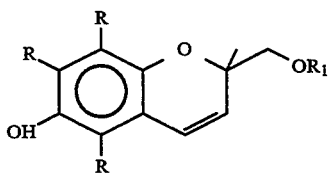
I wherein R denotes a lower alkyl group having 1 to 4 C atoms and R$_1$ denotes a phenyl group which is unsubstituted or substituted by a lower alkyl group having 1 to 4 C atoms, by halogen or by a nitro group, or an alkanoyl group having 1 to 4 C atoms, comprising (a), in the first step, reacting a trialkylhydroquinone of the formula:

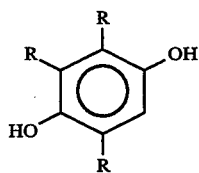
II wherein R has the above-stated meaning with a butenol of the formula:

IIIa or

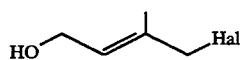
IIIb wherein Hal denotes chlorine, bromine or iodine, in the presence of a Lewis acid selected from the group consisting of iron chloride, tin trifluoromethanesulfonate, boron trifluoride, and a complex compound of boron trifluoride, to give a teraalkylhydroquinone of the formula:

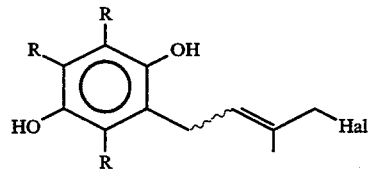
IV wherein R and Hal have the above-stated meanings, (b), in a second step, oxidizing the tetraalkylhydroquinone with air or oxygen to give the quinone of the formula:

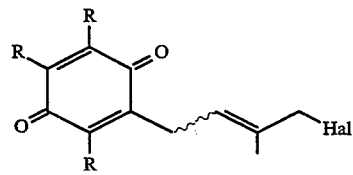
V wherein R and Hal have the above-stated meanings, (c), in a third step, nucleophilically substituting the halogen atom with a nucleophilic compound of the formula:

$(R_1$—$O)_n$M 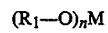 VI wherein R$_1$ has the above-stated meaning, M denotes an alkali metal or alkaline earth metal atom and n is 1 or 2, to give a quinone of the formula:

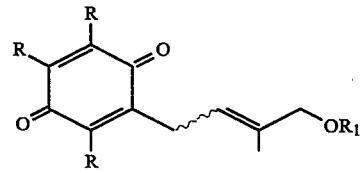
VII wherein R and R$_1$ have the above-stated meanings, and (d), in a fourth step, cyclizing the quinone of the formula I by thermal catalysis, acid catalysis or base catalysis to give the final product of the formula I.

2. The process according to claim 1 wherein the trialkylhydroquinone of the formula II is the trimethyl derivative where R is CH$_3$, and the halogenated butenol derivative is 1-chloro-2-methylbut-3-en-2-ol of the formula IIIa where Hal is Cl.

3. The process according to claim 2 wherein the Lewis acid is boron trifluoride or one of its complex compounds.

4. The process according to claim 3 wherein the reaction to give the tetraalkylhydroquinone is carried out in the presence of an inert solvent at a temperature between −10° and 50° C.

5. The process according to claim 4 wherein the reaction to give the tetraalkylhydroquinone is carried out in such a way that when the starting material trialkylhydroquinone is virtually no longer detectable in the reaction mixture the reaction is immediately stopped and the resulting tetraalkylhydroquinone is isolated.

6. The process according to claim 1 wherein the oxidation with oxygen is carried out at room temperature in the presence of an inert solvent.

7. The process according to claim 1 wherein the nucleophilic substitution in step (c) is carried out in the presence of a phase transfer catalyst.

8. The process according to claim 7 wherein the nucleophilic substitution in step (c) is carried out in a polar solvent at a temperature between 0° C. and the boiling temperature of the solvent.

9. The process according to claim 8 wherein the nucleophilic compound of the formula VI is an alkali metal salt of p-nitrophenol.

10. The process according to claim 7 wherein the phase transfer catalyst is a tetraalkylammonium halide or a tetraalkylphosphonium halide.

11. The process according to claim 1 wherein the cyclization is carried out by base catalysis with a trialkylamine.

12. The process according to claim 1 wherein the nucleophilic substitution in step (c) and the cyclization in step (d) are carried out without isolation of the quinone of the general formula VII.

13. The process according to claim 1 wherein the reaction to give the tetraalkylhydroquinone is carried out in the presence of an inert solvent at a temperature between −10° and 50° C.

14. The process according to claim I wherein the reaction to give the tetraalkylhydroquinone is carried out in such a way that when the starting material trialkylhydroquinone is virtually no longer detectable in the reaction mixture the reaction is immediately stopped and the resulting trialkylbenzene is isolated.

15. The process according to claim 1 wherein the nucleophilic substitution in step (c) is carried out in a polar solvent at a temperature between 0° C. and the boiling temperature of the solvent.

16. The process according to claim 1 wherein, the nucleophilic compound of the formula VI, is an alkali metal salt of p-nitrophenol.

* * * * *